United States Patent
Shaw

(10) Patent No.: US 6,695,870 B2
(45) Date of Patent: Feb. 24, 2004

(54) PROCESS FOR TREATING DISEASE

(75) Inventor: David T. Shaw, East Amherst, NY (US)

(73) Assignee: Nanocomp, L.L.C., East Rochester, NY (US)

( * ) Notice: Subject to any disclaimer, the term of this patent is extended or adjusted under 35 U.S.C. 154(b) by 0 days.

(21) Appl. No.: 10/082,606

(22) Filed: Feb. 25, 2002

(65) Prior Publication Data

US 2003/0163175 A1 Aug. 28, 2003

(51) Int. Cl.[7] .......................... A61N 5/00; A61B 18/18; A61B 19/00; G01T 1/20
(52) U.S. Cl. .............................. 607/88; 607/89; 606/3; 128/898; 250/369 R
(58) Field of Search ................. 606/2, 8, 9; 607/88–91, 607/93, 94; 128/898; 250/369 R, 398–400, 493.1

(56) References Cited

U.S. PATENT DOCUMENTS

| 4,891,043 A | * | 1/1990 | Zeimer et al. ................ 604/20 |
| 5,073,913 A | * | 12/1991 | Martin ......................... 378/34 |
| 5,437,274 A | * | 8/1995 | Khoobehi et al. ........... 128/633 |
| 5,541,947 A | * | 7/1996 | Mourou et al. ................ 372/25 |
| 5,630,786 A | * | 5/1997 | Griffin et al. ................... 600/3 |
| 5,668,371 A |   | 9/1997 | Deasy et al. |
| 5,760,395 A | * | 6/1998 | Johnstone ................... 250/306 |
| 5,944,748 A | * | 8/1999 | Mager et al. .................. 607/88 |
| 6,332,017 B1 | * | 12/2001 | Carroll et al. .............. 378/119 |

* cited by examiner

Primary Examiner—Linda C. M. Dvorak
(74) Attorney, Agent, or Firm—Howard J. Greenwald P.C.

(57) ABSTRACT

A process for treating diseased cells with protons and light nuclei, comprising the steps of: (a) disposing a multiplicity of nanocapsules a biological organism, (b) focusing laser energy at awavelength of from about 350 nanometers to about 850 nanometers and an intensity of from about $10^{19}$ to about $10^{21}$ watts/square centimeter, and (c) contacting the nanocapsules with the focused laser energy for less than about 30 femtoseconds, thereby producing charged nuclei within said capsules.

16 Claims, 3 Drawing Sheets

PROCESS FOR TREATING DISEASE

BACKGROUND OF THE INVENTION

A process for treating a diseased organism in which encapsulated material is disposed within the organism and contacted with focused photonic energy.

BACKGROUND OF THE INVENTION

Proton therapy is often used to treat tumors. Thus, e.g., and as is disclosed in U.S. Pat. No. 5,668,371, "In present proton therapy systems, a beam of protons is collimated to the outline of the tumor and adjusted in energy to stop at the far edge of the tumor. Material is then inserted in the proton beam to reduce the energy of the protons and thus draw the point where the protons stop back through the tumor."

In prior art proton therapy processes, it is difficult to narrowly focus the proton energy on diseased tissue. Thus, as is disclosed in Column 2 of U.S. Pat. No. 5,668,371, "This technique, which continuously exposes the patient to the beam of protons as the spokes are moved through the beam, dramatically increases the dose to healthy tissue on the near side of the tumor . . . ."

It is an object of this invention to provide a process of proton therapy in which the dose of protons supplied to healthy tissue within an organism is minimized.

SUMMARY OF THE INVENTION

In accordance with this invention, there is provided a process for proton therapy comprising the steps of disposing a multiplicity of nanocapsules at a specified site within a biological organism, focusing laser energy at a wavelength of from about 350 nanometers to about 850 nanometers and an intensity of from about $10^{19}$ to about $10^{21}$ watts/square centimeter, and contacting said nanocapsules with said focused laser energy for less than about 30 femtoseconds, thereby producing charged nuclei within said capsules.

BRIEF DESCRIPTION OF THE DRAWINGS

The invention will be described by reference to the following drawings, in which like numerals refer to like elements, and in which.

DESCRIPTION OF THE PREFERRED EMBODIMENTS

Figure 1A:
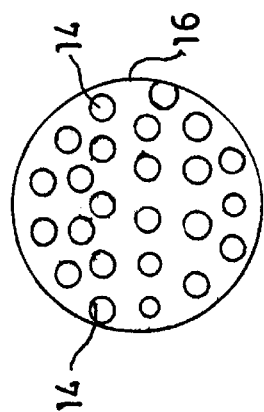
FIG. 1A is an enlarged view of a portion of the nanocapsules utilized in the process depicted in FIG. 1.
Figure 1:
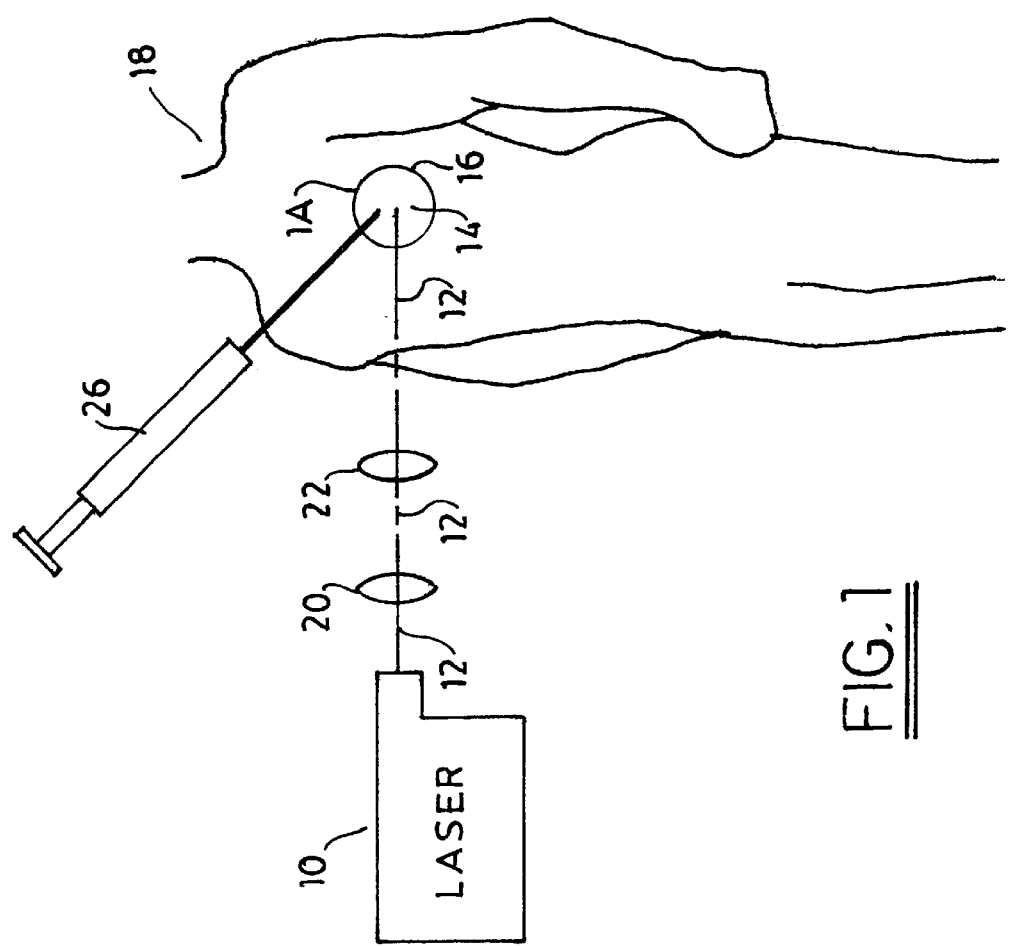
FIG. 1 is a schematic of one preferred process of the invention.

FIG. 1 is a schematic representation of a preferred process of the instant invention. Referring to FIG. 1, it will be seen that a high-power laser 10 produces a laser beam 12 that contacts a multiplicity of nanosized capsules 14 disposed within a diseased organ 16 of a patient 18. FIG. 1A is an enlarged view of apportion of said nanocapsules 14.

The power source 10 used in the process of this invention preferably produces pulsed energy with a pulse duration of short magnitude. Thus, e.g., in one embodiment the laser 10 preferably produces pulses with a duration of less than about 30 femtoseconds. As is known to those skilled in the art, a femtosecond is $10^{-15}$ seconds.

In one embodiment, the laser 10 produces pulses with a duration of from about 10 to about 30 femtoseconds. Femtosecond lasers for producing such pulses are well known. Reference may be had, e.g., to U.S. Pat. No. 6,324,257, the entire disclosure of which is hereby incorporated by reference into this specification. At column 2 of this patent, it is disclosed that "With the development of femtosecond laser, such power densities are achievable with moderate size lasers . . ."

By way of further illustration, one may use one or more of the femtosecond lasers described in U.S. Pat. No. 4,815,080 (laser providing stable femtosecond pulses), U.S. Pat. No. 5,786,560 (micromachining with femtoseocnd laser pulses), U.S. Pat. No. 5,627,848 (device for producing femtosecond and picoseocnd pulses), and the like. The entire disclosure of each of these United States patents is hereby incorporated by reference into this specification.

By way of yet further illustration, one may use the laser described in an article by Koichi Yamakawa et al. on a "Ultrafast, Ultrahigh-Peak, and High-Average Power Ti:Sapphire Laser System" (IEEE Journal of Selected Topics in Quantum Electronics, Volume 6, No. 4, July/August, 2000). The laser described in this article produces mulitera-watt optical pulses in the 10-femtosecond range.

By way of yet further illustration, one may use one or more of the high-powered lasers described in U.S. Pat. Nos. 6,332,017, 5,789,876 (device for producing ultra-short electron pulses), U.S. Pat. Nos. 5,757,839, 5,606,588, 5,419,947, 5,541,947, 5,960,016, 5,656,186, 6,327,068, 6,159,832, 5,825,847, 5,644,424, and the like. The entire disclosure of each of these United States patents is hereby incorporated by reference into this specification.

In one embodiment, the pulses produced by laser 10 are optical pulses with a wavelength of from about 350 to about 850 nanometers. In one aspect of this embodiment, the pulses have a wavelength of from about 750 to about 850 nanometers.

Referring again to FIG. 1, the laser 10 preferably produces from about 1 to about 100 laser pulses per second.

It is preferred that each such pulse produced by laser 10 have a peak power greater than 50 Terawatts. As is known to those skilled in the art, the peak power of an optical pulse is the maximum power of such pulse, which is generally produced at its peak.

Figure 2A:
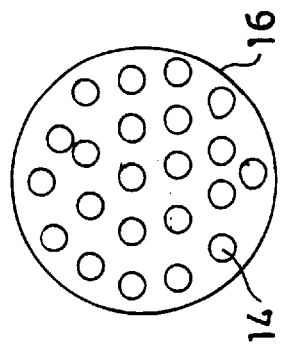
FIG. 2A is an enlarged view of the nanocapulses utilized in the process depicted in FIG. 2.
Figure 2:
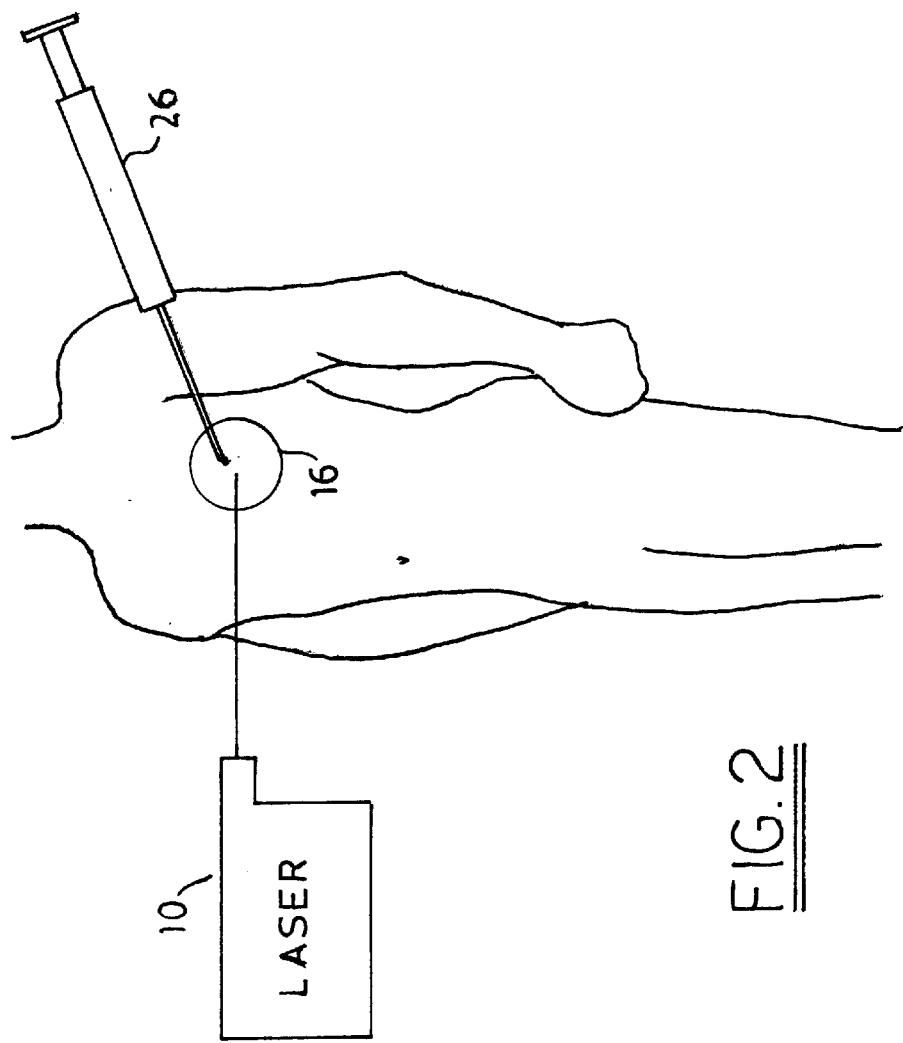
FIG. 2 is a schematic of another preferred process of the invention.

In one embodiment, and referring to the aforementioned Yamakawa et al. article, the laser system used is the front end of a for-stage amplification system that produces peak powers on the order of 20 Joules in 20 femtoseconds; a schematic of this laser is shown in FIG. 2 of such article. The system comprises a 10 femtosecond titanium: sapphire oscillator, a cylindrical mirror-based pulse expander, a regenerative amplifier incorporating regenerative pulse shaping, a four-pass preamplifier, a four-pass power amplifier, and a vacuum pulse compressor.

Referring again to FIG. 1, and in the preferred embodiment depicted therein, the laser beam 12 may be focused by conventional means. Thus, e.g., one may use one or more movable lenses 20 and 22.

In the embodiment depicted in FIG. 1, two lenses (20/22) are used to focus the beam 12. In another embodiment, not shown in this specification but described in the aforementioned Yamakawa et al. publication, the output beam is focused with a 3-meter focal-length spherical mirror.

In yet another embodiment, the output beam is focused by means of the process described in U.S. Pat. No. 5,394,411, the entire disclosure of which is hereby incorporated by reference into this specification. This patent discloses optical guiding of intense laser pulses over a distance of more than one Rayleigh length in a plasma using a multi-pulse technique. The first pulse or pulse sequence prepares a shock-driven, axially-extended radial electron density profile which guides a second pulse or sequence of pulses. The profile is also capable of guiding x-rays. The channel will support mode structure exactly analogous to that of an optical fiber waveguide. The method provides a means for guiding of a high intensity optical laser pulse or x-rays over distances well in excess of a Rayleigh length. The distances over which guiding occurs is limited only by the length of the preformed plasma and absorption and possible backscattering of the guided EM radiation. Applications of the method allow for compact x-ray laser devices and electron particle accelerators.

In particular, U.S. Pat. No. 5,394,411 claims: ". A method of guiding intense electromagnetic (EM) radiation pulses over a distance of more than one Rayleigh length for a device requiring high intensity laser induced processes in a plasma produced in a first medium surrounded by a second medium in at least a first chamber, the method comprising the steps of: supplying at least one first laser pulse to the first medium by a first laser source means whereby the at least one first laser pulse produces a plasma in the first medium generating a pressure gradient between the plasma and the second medium; generating a shock wave which in turn induces a refractive index profile channel greater than one Rayleigh length in the plasma; and supplying at least a single second EM pulse with an appropriate delay from the at least one first laser pulse by a second EM source means along the axis of the refractive index profile channel of the plasma for transmission through the plasma whereby the channel performs as a plasma EM waveguide."

It is preferred that the spot size of the focused beam 12, i.e., its diameter, be from about 1 microns to about 1 centimeter. In one preferred embodiment, such spot size is from about 2 to about 20 microns. In another embodiment, the spot size of the focused pulses are from about 2 to about 4 microns. One may use conventional means of producing laser outputs with specified spot sizes. Reference may be had, e.g., to U.S. Pat. No. 6,324,179 (means for producing adjustable laser spot size), U.S. Pat. No. 4,601,037 (pulsed laser spot size adjustment), U.S. Pat. Nos. 4,590,598, 3,769, 963 (device for performing laser microsurgery), U.S. Pat. No. 5,631,687, and the like. The entire disclosure of each of these United States patents is hereby incorporated by reference into this specification.

Referring again to FIGS. 1 and 1A, and in the preferred embodiment depicted therein, the laser beam 12 is focused upon a multiplicity of nanocapsules 14. These nanocapsules 14 may be produced by conventional means.

In one embodiment, the nanocapsules 14 have diameters of from about 50 to about 5,000 nanometers and, more preferably, from about 100 to about 500 nanometers. In this embodiment, the nanocapsules are mixed with liquid, preferably in a concentration of from about 10 to about 50 volume percent, by total volume of capsules and liquid.

One may prepare dispersible colloidal systems comprised of nanocapsules in accordance with conventional techniques. Thus, e.g., by way of illustration and not limitation, one may use the process described in U.S. Pat. No. 5,049, 322 of Devissagujet et al. This patent describes and claims: "A process for the preparation of dispersible colloidal systems in the form of spherical particles of the vesicular type and of a size less than 500 nm (nanocapsules), the wall of which is constituted by a substance A having film-forming properties and the core by a liquid substance B capable of being encapsulated by the substance A, comprising: combining (1) a first liquid phase consisting essentially of a solution of the substances A and B in a solvent for the substances A and B or in a mixture of solvents for the substances A and B, and (2) a greater amount of a second liquid phase consisting essentially of a non-solvent or a mixture of non-solvents for the substances A and B and including one or more surfactants, the solvent or the mixture of solvents of the first phase being miscible in all proportions with the non-solvent or mixture of non-solvents of the second phase, comprising a core of said liquid substance B surrounded by a layer of said substance A."

By way of further illustration, one may prepare disperse colloidal systems of nanocapsules in accordance with the process described and claimed in U.S. Pat. No. 5,705,196; the entire disclosure of such United States patent is hereby incorporated by reference into this specification. This patent describes and claims: ". A continuous method for preparing nanospheres comprising: (1) mixing under constant stirring and controlled temperature and pH (a) an aqueous phase comprising water, and optionally, one or more surface active agents and suspensor agents wherein said agents are, optionally, chemically or biologically active substances; and (b) an organic phase comprising a solve or a mixture of solvents each having a miscibility in water of greater than 10% or a dielectric point of greater than 15, a biocompatible polymer or monomer or a mixture thereof, and, optionally, a lipid product and a chemically or biologically active substance; (c) wherein the mixing continues until the desired phase ratio and reaction medium volume are obtained and a colloid suspension is formed; (2) continuously removing the colloid suspension and continuously adding further organic and aqueous phases such that the desired phase ratio and reaction medium volume are maintained; (3) introducing the removed colloidal suspension to an evaporator where the organic solvent is continuously removed; and (4) withdrawing the resultant organic solvent-free suspension including nanospheres from the evaporator."

Thus, by way of further illustration, one may prepare the nanocapsules 14 by one or more of the means disclosed in U.S. Pat. No. 4,891,043, the entire disclosure of which is hereby incorporated by reference into this specification. As is disclosed in Column 1 of this patent, " . . . lipid vesicles, known as liposome's, have come into use in recent years. The lipid vesicles encapsulate drugs or dyes and can be injected into the bloodstream where they are carried to various organs in which they are naturally ruptured and the encapsulated materials released. The manner of making lipid vesicles is disclosed in, for example, U.S. Pat. No. 4,078,052 . . . and U.S. Pat. No. 4,241,046 . . . ."

By way of further illustration, one may prepare nanocapsules by one or more of the methods disclosed in U.S. Pat. No. 5,437,274, the entire disclosure of which is hereby incorporated by reference into this specification. As is disclosed at Columns 5 and 6 of this patent, "The fluorescent dye in one embodiment of the invention is encapsulated by a vesicle or particle such that the dye is contained in the solid or liquid core of the vesicle or particle. For example, the fluorescent dye can be encapsulated in the aqueous core of liposomes. In alternative embodiments, the fluorescent dye can be incorporated within the particle or vesicle, such as in the cell wall of a microcapsule or in the lipophilic layer of a liposome. The fluorescent dye as used herein may be any dye that is capable of fluorescing when subjected to light within the wavelength produced by the laser. In preferred embodiments, the fluorescent dye is selected from the group consisting of calcein, carboxfluorescein, sodium fluorescein and indocyanine green. Indocyanine green fluoresces when subjected to light in the infrared spectral range. Calcein, carboxyfluorescein and sodium fluorescein fluoresce when subjected to light in the blue and blue-green part of the electromagnetic spectrum. The concentration of the fluorescent dye in the vesicles or particles is preferably sufficiently high so that the vesicles or particles fluoresce and become visible when subjected to the laser energy. The concentration preferably is not sufficient to quench the fluorescent properties of the dye. In one preferred embodiment of the invention, the fluorescent dye is encapsulated in lipid vesicles known as liposomes. Liposomes, as known in the art, are vesicles made from phospholipids defining a lipid phase that encapsulates an aqueous phase. The fluorescent dye is preferably encapsulated in the aqueous phase although the dye may be dispersed in the lipid phase. The liposomes in accordance with preferred embodiments are advantageously prepared from dipalmitoylphosphatidylglycerol (DPPG) and dipalmitoylphosphatidylcholine (DPPC). The lipid wall can be strengthened when needed by the use of cholesterol in the lipid phase to prevent leakage of the lipid wall. The phospholipids used to encapsulate the dye preferably have a transition temperature of below 37° C., such as phosphatidylcholine. In preferred embodiments, the phospholipids have a transition temperature below 37° C. by using the phospholipid in combination with cholesterol. The liposomers have a size of about 0.02 to 2.0 microns and preferably less than 1.0 micron. When phospholipids have a transition temperature above 37° C., the cholesterol is usually not necessary."

"The liposomes may be prepared by dispersing the fluorescent dye in the aqueous phase and mixing with the phospholipid. The organic phase is then removed from the mixture. The fluorescent dye is dispersed in the aqueous phase in the amount of about 0.2–2.0 mmol. Calcein, carboxyfluorescein and sodium fluorescein fluoresce effectively in the liposomes at a concentration of about 0.5–2 mmol. Indocyanine green fluoresces at a concentration in the liposomes of about 0.2–1.0 mmol. In alternative embodiments, the concentration of the fluorescent dye can be sufficiently high to quench the fluorescent properties of the dye provided walls of the liposome permit some of the dye to diffuse outward. It has been found that the dye which diffuses through the outer wall adhere to the outer surface at a concentration to fluoresce when subjected to light of the appropriate wavelength. Numerous other methods of preparing liposomes may also be used as recognized by one skilled in the art."

"Other phospholipids which can be used to prepare the liposomes include egg phosphatidylcholine (EPC), dilauryloylphosphatidylcholine (DLPC), dimyristoylphosphatidylcholine (DOPC), distearoylphosphatidylcholine (DSPC), DSPE-PEG-2000,1-myristoyl-2-palmitoylphosphatidylcholine (MPPC), 1-palmitoyl-2-myristoyl phosphatidylcholine (PMPC), 1-palmit-oyl-2-stearoyl phosphatidylcholine (PSPC), 1-stearoyl-2palmitoyl phosphatidylcholine (SPPC), dioleoylphosphatidylycholine (DOPC), dilauryloylphosphatidylglycerol (DLPG), dimyristoylphosphatidylglycerol(DMPG), dipalmitoylphosphatidylglycerol (DPPG), distearoylphosphatidylglycerol (DSPG), dioleoylphosphatidylglycerol (DOPG), dimyristoyl phosphatidic acid (DMPA), dipalmitoyl phosphatidic acid (DPPA), dimyristoyl phosphatidylethanolamine (DMPE), dipalmitoyl phosphatidylethanolamine (DPPE), dimyristoyl phosphatidylserine (DMPS), dipalmitoyl phosphatidylserine (DPPS), brain phosphatidylserine (PS), brain sphingomyelin (BSP), dipalmitoyl sphingomyelin (DPSP), distearoyl sphingomyelin (DSSP), disteroylphosphatidylcholine (DSPC), dimyristolphosphatidylcholine and dipalmitoyl phosphatidylethanolamine."

"The liposomes can be unilamellar or multilamellar made by known procedures. Procedures which can be used are disclosed in U.S. Pat. No. 4,235,871 to Papahadjopoulos et al. and U.S. Pat. No. 4,522,803 to Lenk et al. In further embodiments of the invention, the liposomes also contain at least one drug to treat a disorder. The drug may be entrapped in either the aqueous layer or the lipid layer. Examples of suitable drugs include anticoagulants and antibiotics."

"The nanocapsules are also prepared according to conventional procedures as known in the art. These nanocapsules comprise a liquid or solid core encapsulated by a continuous wall of a water insoluble membrane of a synthetic polymer. The nanocapsules have a size of about 0.1–0.4 microns. The nanocapsules may be prepared, for example, by the process described in Fessi et al., Nanocapsule Formation by Interfacial Polymer Deposition Following Solvent Displacement, International Journal of Pharmaceutics, 55 (1989) R1–R4. The process includes dissolving a known amount of poly,(D,L lactide) polymer in acetone. A known amount of a phospholipid is dissolved in acetone by heating close to the boiling point. An aqueous solution of a fluorescent dye is then added to the acetonic solution. The resulting organic solution is poured into a known amount of water containing poloxamer while stirring. The poloxamer is a highly water soluble surfactant needed for physical stability of the nanocapsule suspension. The acetone rapidly diffuses toward the aqueous phase and is removed under reduced pressure. The resulting colloidal suspension if concentrated to the desired final volume by the removal of water. In alternative processes, the nanocapsules may be prepared from other polymers such as polyinylacetate, polyvinylchloride, poly E-caprolactone and ethylcellulose."

"Microspheres and nanospheres are formed from polymers and copolymers forming an encapsulating outer wall and an aqueous or other liquid core or a solid core. Microspheres are 2.0–4.0 microns, while nanospheres are less than 1.0 micron. The microspheres in preferred embodiments have a diameter of up to about 2.0 microns. Suitable polymers include, for example, polylactic acid, polyglycolic acid and copolymers thereof, ethylene-vinyl acetate, polyanhydrides, polyamides, and orthoesters. The microcapsules may be prepared according to known methods, such as the methods disclosed in U.S. Pat. No. 4,997,652 to Wong and Bindschaedler et al., Polyanhydride Microsphere Formulation by Solvent Extraction, Journal of Pharmaceutical Sciences, Vol. 77, no. 8, August 1988."

By way of further yet illustration, one may make the nanocapsules 14 by the means disclosed in U.S. Pat. No. 5,5000,224, the entire disclosure of which is hereby incorporated by reference into this specification. This patent discloses and claims: "A pharmaceutical composition in the form of a colloidal suspension of nanocapsules, comprising an oily phase consisting essentially of an oil, wherein the oil is a vegetable oil, a mineral oil or an oily compound selected from benzyl benzoate and glycerides of higher fatty acids, said oil containing dissolved therein a surfactant and, suspended therein, a plurality of nanocapsules having a diameter of less than 500 nanometers, said nanocapsules encapsulating an aqueous phase consisting essentially of a solution or a suspension of a therapeutically active substance and a surfactant in water, whose pH lies between 1 and 7, whereby the walls of said nanocapsules are formed from a poly(alkyl 2-cyanoacrylate) wherein the alkyl radical has 1 to 6 carbon atoms, all constituents of said composition being chosen from pharmaceutically acceptable substances."

One may use any conventional means for delivering the nanocapsules 14 to a desired site within the living organism 18. Reference may be had, e.g., to U.S. Pat. Nos. 5,976,502 (treatment of retina of an eye), U.S. Pat. No. 5,437,274 (treatment of blood), U.S. Pat. No. 5,993,831 (treatment of epidermis), U.S. Pat. No. 5,360,610 (treatment of nerve fiber), U.S. Pat. No. 5,693,532 (treatment of respiratory system) and the like. The entire disclosure of each of these United States patents is hereby incorporated by reference into this specification.

In one embodiment, one may use the administration means disclosed in U.S. Pat. No. 6,033,645, the entire disclosure of which is hereby incorporated by reference into this specification. Particular reference may be had to FIG. 1 of this patent, which illustrates " . . . a schematic representation of a system agent to a patient in accordance with an embodiment of the present invention. The apparatus 12 includes a first vessel which, in FIG. 1, is depicted as a syringe 14 consisting of a barrel 16 and a plunger 18 which is slidably engaged with the barrel 16. A contrast agent 20, such as, for example, a vesicle composition as described hereinabove, is contained in the syringe 14. The apparatus 12 further comprises a second vessel which, in accordance with the presently preferred embodiment, comprises a mechanical injector 22. A device which is particularly suitable for use as the mechanical injector 22 is a MedRad.TM. Power Injector (Medrad, Inc., Pittsburgh, Pa.). The mechanical injector 22 preferably contains a flush agent 24, such as saline. As shown in FIG. 1, the syringe 14 and the mechanical injector 22 are in flow communication with each other via a conduit 26. The conduit 26 is preferably adapted to administer the contrast agent 20 and/or flush agent 24 to a patient 28 (shown schematically). The conduit 26 preferably comprises tubing 30, which may comprise any suitable sterile plastic tubing, and a needle 32. Means are provided for connecting the syringe 14 and the mechanical injector 22 with the tubing 30 which places the syringe 14 and the mechanical injector 22 in flow communication with each other. In accordance with the presently preferred embodiment, the flow communication means comprises a 3-way stopcock 34 which is engaged to the needle 32 and the tubing 30 and is located below the syringe 14. The stopcock 34 comprises a housing 36 and a valve 38. As shown in FIG. 1, a nozzle 40 is also provided on the mechanical injector 22 to which the tubing 30 is connected. Also provided in the apparatus 12 is a control means 42, shown in schematic form, for controlling the mechanical injector 22. The control means 42 controls the amount of power supplied to the mechanical injector 22 and permits regulation of the rate at which the mechanical injector 22 operates and, thereby, the rate at which the flush agent 24 is ejected from the mechanical injector 22."

By way of further illustration, other means for administering the nanocapuses to a biological organism are described, e.g., in U.S. Pat. No. 5,916,596 (in vivo delivery of water insoluble pharmacogically active agents). By way of further illustration, one may deliver the nanocapsules to a tumor by one or more of the conventional means used to deliver magnetic particles to a tumor. In one aspect of this embodiment, the nanocapsules can be made magnetic.

Figure 3A:
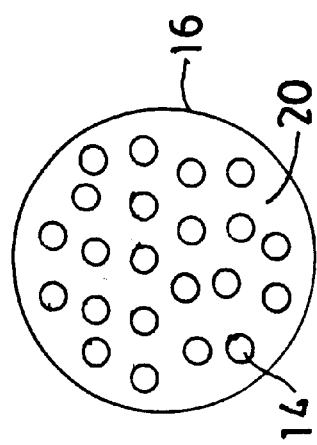
FIG. 3A is an enlarged view of the nanocupsules utilized in the process depicted in FIG. 3.
Figure 3:
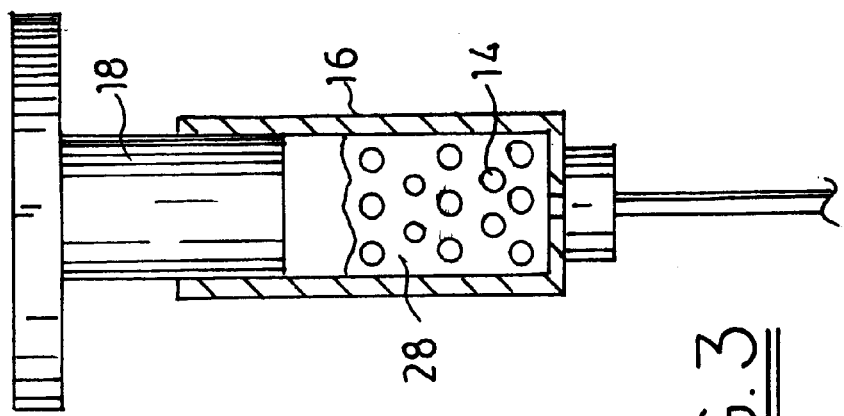
FIG. 3 is a schematic of one preferred means of disposing nanocapsules within a human body.

In the preferred embodiments illustrated in FIGS. 1, 2, and 3, a syringe 26 is used to dispose the nanocapsules 14 near or in the organ 16. In the embodiment depicted in FIG. 3, the nanocapsules are preferably dispersed in a liquid 28.

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention as defined in the following claims.

I claim:

1. A process for treating diseased cells with protons and light nuclei, comprising the steps of:

(a) disposing a multiplicity of nanocapsules in a biological organism, (b) focusing laser energy at a wavelength of from about 350 nanometers to about 850 nanometers and an intensity of from about $10^{19}$ to about $10^{21}$ watts/square centimeter, and (c) contacting said nanocapsules with said focused laser energy for less than about 30 femtoseconds, thereby producing charged nuclei within said capsules.

2. The process as recited in claim 1, wherein said laser beam is focused within a plasma disposed within a waveguide.

3. The process as recited in claim 2, wherein a said plasma disposed within said waveguide is produced by a shock wave.

4. The process as recited in claim 3, wherein said nanocapsules are contacted with said focused laser energy for from about 10 to about 30 femtoseconds.

5. The process as recited in claim 4, wherein said focused laser energy has a wavelength of from about 750 to about 850 nanometers.

6. The process as recited in claim 5, wherein said focused laser energy is pulsed focused laser energy.

7. The process as recited claim 6, wherein said pulsed focused laser energy is comprised of from about 1 to about 100 laser pulses per second.

8. The process as recited in claim 7, wherein each of said pulses has a peak power greater than 50 Terawatts.

9. The process as recited in claim 8, wherein each pulsed focused laser energy has a spot size of from about 1 micron to about 1 centimeter.

10. The process as recited in claim 9, wherein said spot size is from about 2 to about 20 microns.

11. The process as recited in claim 9, wherein said spot size is form about 2 to about 4 microns.

12. The process as recited in claim 9, wherein each of said nanocapsules has a diameter of from about 50 to about 5,000 nanometers.

13. The process as recited in claim 9, wherein each of said nanocapsules has a diameter of from about 100 to about 500 nanometers.

14. The process as recited in claim 12, wherein nanocapsules are mixed with a liquid to provide a dispersed nanocapsules system.

15. The process as recited in claim 12, wherein each of said nanocapsules is comprised of a core encapsulated by a continuous, water-insoluble membrane.

16. The process as recited into claim 12, wherein said nanocapsules are injected into said biological organism.

* * * * *